United States Patent
D'Amelio et al.

(10) Patent No.: US 7,878,972 B2
(45) Date of Patent: Feb. 1, 2011

(54) REMOVABLE OPTICAL ASSEMBLY FOR A MEDICAL INSTRUMENT

(75) Inventors: Frank D'Amelio, Los Olivos, CA (US); Gregory Konstorum, Stamford, CT (US); Anthony Mazurkewitz, Danbury, CT (US)

(73) Assignee: Gyrus ACMI, Inc., Southborough, MA (US)

( * ) Notice: Subject to any disclaimer, the term of this patent is extended or adjusted under 35 U.S.C. 154(b) by 1243 days.

(21) Appl. No.: 11/109,024

(22) Filed: Apr. 18, 2005

(65) Prior Publication Data
US 2005/0182299 A1    Aug. 18, 2005

Related U.S. Application Data

(63) Continuation of application No. PCT/US03/32975, filed on Oct. 17, 2003.

(60) Provisional application No. 60/419,544, filed on Oct. 18, 2002.

(51) Int. Cl.
*A61B 1/06* (2006.01)
(52) U.S. Cl. .................. 600/172; 600/129; 600/133; 600/136; 600/175; 600/176
(58) Field of Classification Search ............. 600/129, 600/133, 161, 175–176; 359/819, 829
See application file for complete search history.

(56) References Cited

U.S. PATENT DOCUMENTS

| | | | | |
|---|---|---|---|---|
| 4,905,670 A | | 3/1990 | Adair | |
| 5,325,847 A | * | 7/1994 | Matsuno | 600/109 |
| 5,569,157 A | * | 10/1996 | Nakazawa et al. | 600/107 |
| 5,570,237 A | * | 10/1996 | Sato | 359/797 |
| 5,685,823 A | * | 11/1997 | Ito et al. | 600/127 |
| 5,700,236 A | | 12/1997 | Sauer et al. | |
| 5,868,664 A | | 2/1999 | Speier et al. | |
| 5,871,440 A | * | 2/1999 | Okada | 600/129 |
| 5,961,445 A | * | 10/1999 | Chikama | 600/112 |
| 6,030,339 A | | 2/2000 | Tatsuno et al. | |
| 6,063,023 A | * | 5/2000 | Sakiyama et al. | 600/118 |
| 6,122,115 A | * | 9/2000 | Plummer et al. | 359/822 |
| 6,184,923 B1 | | 2/2001 | Miyazaki | |

(Continued)

FOREIGN PATENT DOCUMENTS

DE            1122738            1/1962

(Continued)

OTHER PUBLICATIONS

International Search Report (PCT), Jul. 9, 2004, ACMI Corp.

(Continued)

*Primary Examiner*—Matthew J Kasztejna
(74) *Attorney, Agent, or Firm*—Ganz Law, P.C.

(57) ABSTRACT

An optical probe, for example, a medical endoscope, having a removable lens cell. In an embodiment, the optical probe has an elongated tube with a proximal portion terminating at a proximal end and a distal portion opposite the proximal portion terminating at a distal end. The elongated tube defines an axial lumen wherein a lens cell holder is disposed proximal the distal portion. The lens cell holder has an axial holder bore for at least partially containing the lens cell within and removably coupled with the holder bore.

4 Claims, 9 Drawing Sheets

U.S. PATENT DOCUMENTS

| | | | |
|---|---|---|---|
| 6,390,972 | B1 | 5/2002 | Speier et al. |
| 6,547,722 | B1 * | 4/2003 | Higuma et al. ............... 600/133 |
| 6,554,767 | B2 * | 4/2003 | Tanaka ........................ 600/175 |
| 6,565,505 | B2 * | 5/2003 | Ishibiki ....................... 600/133 |
| 6,589,165 | B2 * | 7/2003 | Bodor et al. ................ 600/172 |
| 6,605,035 | B2 * | 8/2003 | Ando et al. ................. 600/127 |
| 6,695,775 | B2 * | 2/2004 | Watanabe et al. ........... 600/176 |
| 6,955,644 | B2 * | 10/2005 | Forkey et al. ............... 600/133 |
| 2004/0019255 | A1 | 1/2004 | Sakiyama |
| 2006/0222300 | A1 | 10/2006 | Frenzel et al. |

FOREIGN PATENT DOCUMENTS

| | | |
|---|---|---|
| DE | 4133493 A1 | 4/1992 |
| DE | 10252446 | 5/2004 |
| DE | 10344768 | 8/2005 |
| GB | 906278 | 8/1960 |
| JP | 62-066220 A | 3/1987 |
| JP | 01-136629 A | 5/1989 |
| JP | 04-295327 A | 10/1992 |

OTHER PUBLICATIONS

English translation of German Patent Office Examination Report issued for corresponding German Patent Application No. 10393045.0; 8 pages.

Office action from the Patent Office of Germany dated Feb. 2, 2010 for related German patent application No. 102008018922.7; 4 pages.

English Translation of Office action from the Patent Office of Germany dated Feb. 2, 2010 (previously submitted in the German language in a prior IDS on Mar. 10, 2010) for related German patent application No. 102008018922.7; 4 pages.

* cited by examiner

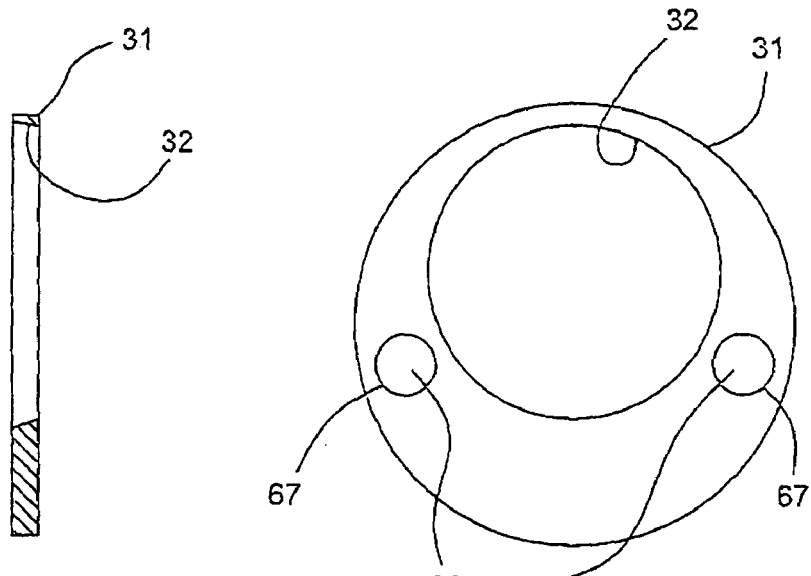
Fig 9A
Fig 9B
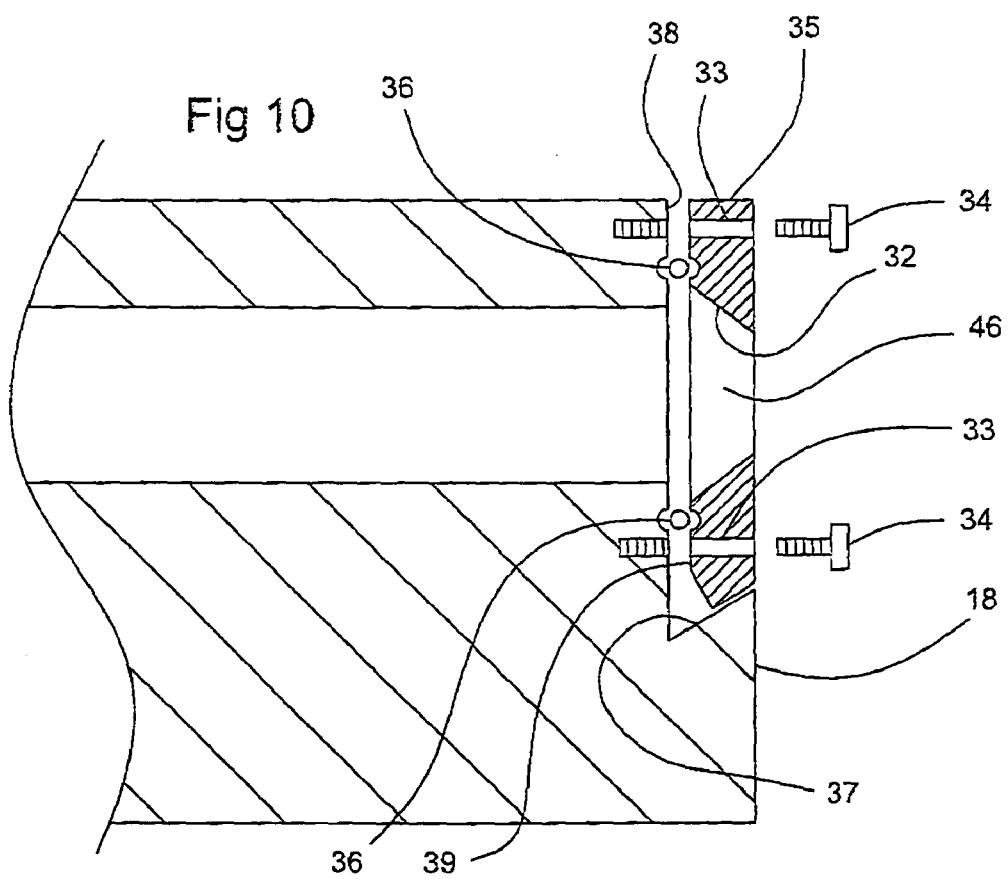
Fig 10

REMOVABLE OPTICAL ASSEMBLY FOR A MEDICAL INSTRUMENT

RELATED APPLICATION

This application is a continuation of PCT/US03/032975, filed Oct. 17, 2003 which claims the benefit of U.S. Provisional Patent No. 60/419,544, filed Oct. 18, 2002, the content of which are hereby incorporated by reference as if recited in full herein for all purposes.

FIELD OF THE INVENTION

This invention relates to medical endoscopes, and, more specifically, to removable and replaceable optical systems for an endoscope's distal end objective head.

BACKGROUND OF INVENTION

An endoscope is a medical device comprising an optical system within an elongated insertion member. Endoscopy refers to procedures wherein an endoscope is used to visualize and/or treat the interior of the body by passing the distal end of the endoscope through an opening or passage. Endoscopes are provided in various configurations suitable for specific procedures. For example, a laparoscope is an endoscope used to visualize and/or treat the interior of the body by passing the distal end of the endo scope through a small incision such as to allow a health care provider to look directly at the outside of abdominal and pelvic organs, including the fallopian tubes, ovaries, uterus, small bowel, large bowel, appendix, liver, and gallbladder. Similiarly, a ureteroscope is an endoscope that may be passed through the ureter to inspect or treat anatomical structure proximate the ureter.

FIG. 1 illustrates an endoscope system 1 known in the art comprising an endoscope 2, a light/signal cable 12, a light source 3, a video processor 4, and a monitor 5. The light source 3 provides illumination through the endoscope 2 to a target so that the endoscope 2 can generate an image signal which is communicated to the video processor 4 for viewing on the monitor 5.

The endoscope 2 comprises an insertion member 10 and a grip 11. The insertion member 10 comprises an elongated tube 8 comprising a proximal portion 15 terminating at a proximal end 16 and a distal portion 17 opposite the proximal portion 15, terminating at a distal end 18. The insertion member 10 can be made flexible or rigid depending on the type of endoscope 2.

FIG. 2 is a side cross-sectional view of the distal end portion 17 of the endoscope 2 that houses an imaging system 6, in accordance with the embodiment of FIG. 1. The imaging system 6 comprises an imaging sensor 24, an electronic substrate 25 and a signal cable 28. The imaging sensor 24 converts the optical image to an image signal which is communicated along the signal cable 28 to the light/signal cable 12 and to the video processor 4. There are a variety of available imaging sensors 24, such as, but not limited to, charged coupled device (CCD) and complementary metal-oxide semiconductor (CMOS) imaging sensors 24.

The grip 11 is coupled to the proximal end 16 of the insertion member 10 and is used to manipulate the insertion member 10 within the body. The light/signal cable 12 couples with and extends from the grip 11 and provides a flexible connection to the light source 3 and the video processor 4. A connector 14 fixed to the end of the light/signal cable 12 is adapted to removably couple with the light source 3 and the video processor 4. Illumination from a lamp (not shown) in the light source 3 is propagated over the light/signal cable 12 and through a light guide 9 within and extending through the endoscope 2 to the distal end 18 to a target to be observed. In some endoscopes 2, illumination is provided by a light source located at the distal end 18. Suitable light sources 3 include, but are not limited to, a solid-state light source comprising light emitting diodes (LED).

The video processor 4 converts the image signal to a video signal that is communicated to a connected monitor 5. Consequently, an endoscopic image is displayed on the monitor 5 and/or collected by a data recorder (not shown).

The distal end portion 17 of the endoscope 2 houses an objective head 30. The objective head 30 comprises optical components that project and focus an image onto the image sensor 24. The objective head 30 comprises an optical window 21, one or more optical elements 22 in a fixed lens cell 26, and a prism 23 to turn the image path 90 degrees as a mirror. The prism 23 is positioned adjacent to the imaging sensor 24.

The fixed lens cell 26 is adhered to the tube lumen 13 and/or cemented directly to the prism 23 using a permanent adhesive 29. An adhesive resistive to high temperature is used to enable high-pressure steam sterilization of the endoscope 2. However, the fixed lens cell 26 cannot be removed from the distal end portion 17 in order to replace the optical elements 22 without risking significant damage to the distal end portion 17, the objective head 30, and/or the imaging system 6. The use of high temperature to crack the adhesive bond can be damaging to the endoscope 2. Mechanical force directed at cracking the adhesive bond also has a high risk of significant damage to the endoscope 2.

A conventional endoscope 2 has one objective head 30 that is not removable, and therefore, is limited to providing fixed optical properties. Endoscopic surgery commonly requires both a wide angle image and a magnified image. The wide angle image is used for finding an organ, a disease, and gross visualization, whereas a magnified image is used for treatment. A wide angle image can be electronically magnified, but the image degrades significantly with increased magnification. Therefore, it is common that more than one endoscope is used for a particular procedure, leading to increased medical costs.

The increased use of endoscopic diagnostic and treatment procedures is putting a greater burden on the health care industry to contain cost, especially when multiple endoscopes are required, each employing specific optical components suitable for a specific visualization or treatment technique. Endoscopes are sterilized and reused, but have a finite lifetime requiring eventual disposal of expensive, high precision components.

Attempts have been made to remove the optical elements from the insertion member, but not without having to disassemble major components of the endoscope, risking damaging the components, and enduring time-consuming processes. Of particular concern is the breaking of the cement bond between the prism and the lens cell in order to remove the optical elements. This results not only in the issues already mentioned regarding disassembly, but requires a time-consuming process to reassemble and align the lens cell and prism.

Accordingly, there is a need to provide endoscopes having objective heads that provide for relatively easy lens cell removal and reassembly without the negative consequences described. These features will allow for maintenance and refurbishment of endoscopes reducing the costs associated with their use.

SUMMARY OF THE INVENTION

The present invention overcomes the aforementioned problems of the current art. One aspect of the present invention provides an optical probe having an elongated tube with a proximal portion terminating at a proximal end and a distal portion opposite the proximal portion terminating at a distal end. The elongated tube defines an axial lumen wherein a lens cell holder is disposed proximal the distal portion. The lens cell holder has an axial holder bore for at least partially containing the lens cell within and removably coupled with the holder bore. Another aspect of the present invention provides an endoscope having an insertion member extending from a handle, the insertion member having an elongated tube with a proximal portion terminating at a proximal end and a distal portion opposite the proximal portion terminating at a distal end, and an axial lumen extending therebetween, the handle coupled to the proximal end. An imaging system is disposed within the lumen proximal the distal portion. The imaging system includes an imaging sensor. An objective head is disposed within the lumen proximal the distal end comprising a lens cell and a lens cell holder, the lens cell at least partially removably coupled with at least a portion of the lens cell holder.

Another aspect of the present invention provides an objective head for an endoscope having a lens cell removably coupled within a lens cell holder.

Another aspect of the present invention provides a removable lens cell for an endoscope. The lens cell comprises a housing adapted for mounting optical components therein, and the housing is adapted for removable engagement with the endoscope distal end.

The present invention also contemplates related methods of manufacturing, used, servicing.

The foregoing is not intended to be an exhaustive list of the novel features of the present invention; these and other novel features of the present invention are described below in more detail.

BRIEF DESCRIPTION OF THE DRAWINGS

FIGS. 9A and 9B are side cross-sectional and front views of a window holder in accordance with an embodiment of the present invention;

FIG. 10 is a side cross-sectional view of a distal end of an insertion member with another window holder in accordance with an embodiment of the present invention;

DETAILED DESCRIPTION OF THE INVENTION

In the following detailed description, reference is made to the accompanying drawings that form a part hereof wherein like numerals designate like parts throughout, and in which is shown by way of illustration specific embodiments in which the invention may be practiced. It is to be understood that other embodiments may be utilized and structural or logical changes may be made without departing from the scope of the present invention. Therefore, the following detailed description is not to be taken in a limiting sense, and the scope of the present invention is defined by the appended claims and their equivalents.

The following embodiments and figures refer to a medical instrument known as an endoscope. The term "endoscope" is used herein a general sense and in accordance with the art, and include, for example, but not limited to, laparoscope, ureteropyeloscope, cystonephroscope, and cystoureteroscope, and medical instruments of substantially similar design. Embodiments in accordance with apparatus and methods of the present invention relate to optical components that are adapted to be removable from the "objective head" of an endoscope without significant damage to the endoscope.

Figure 3A:
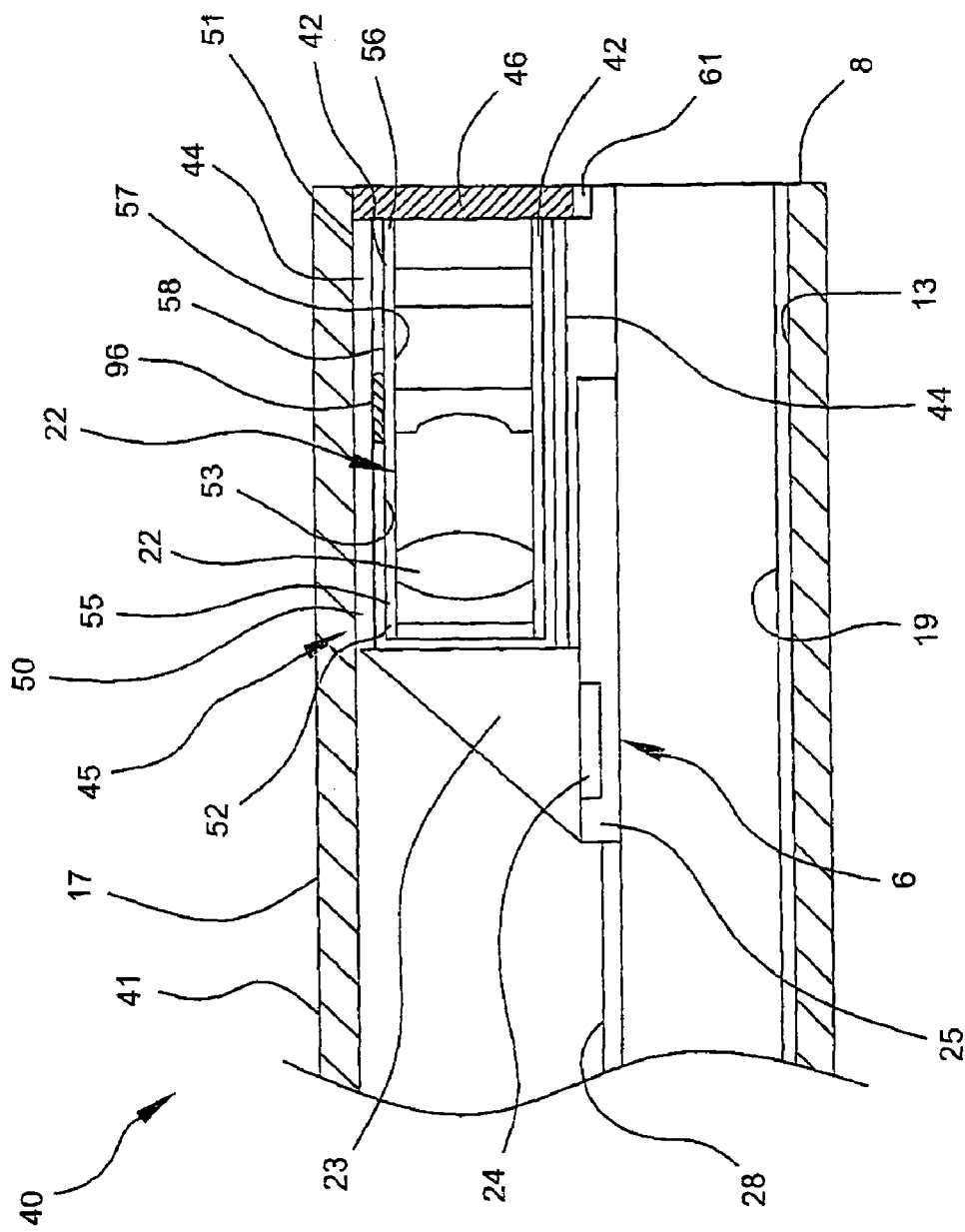
FIGS. 3A and 3B are side cross-sectional and front views of a distal portion of an insertion member, in accordance with an embodiment of the present invention.
Figure 3B:
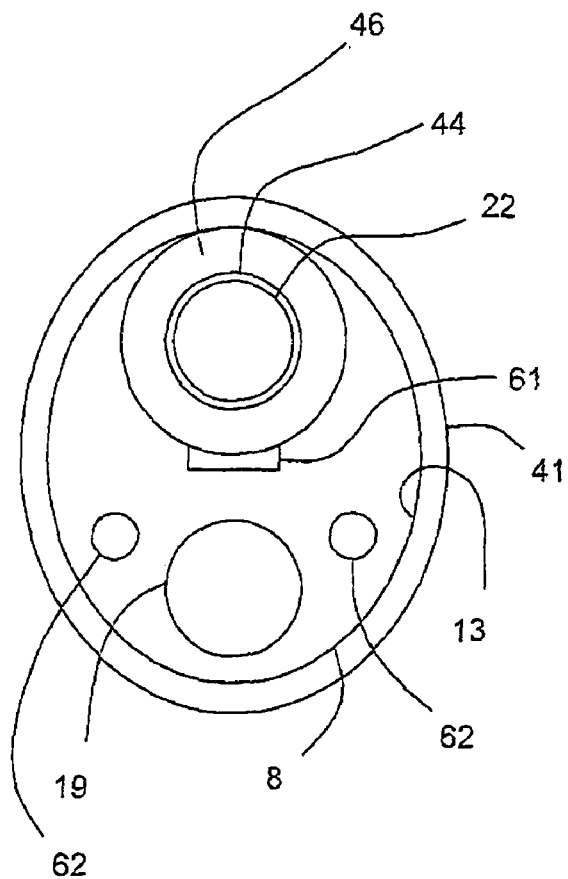
Figure 4:
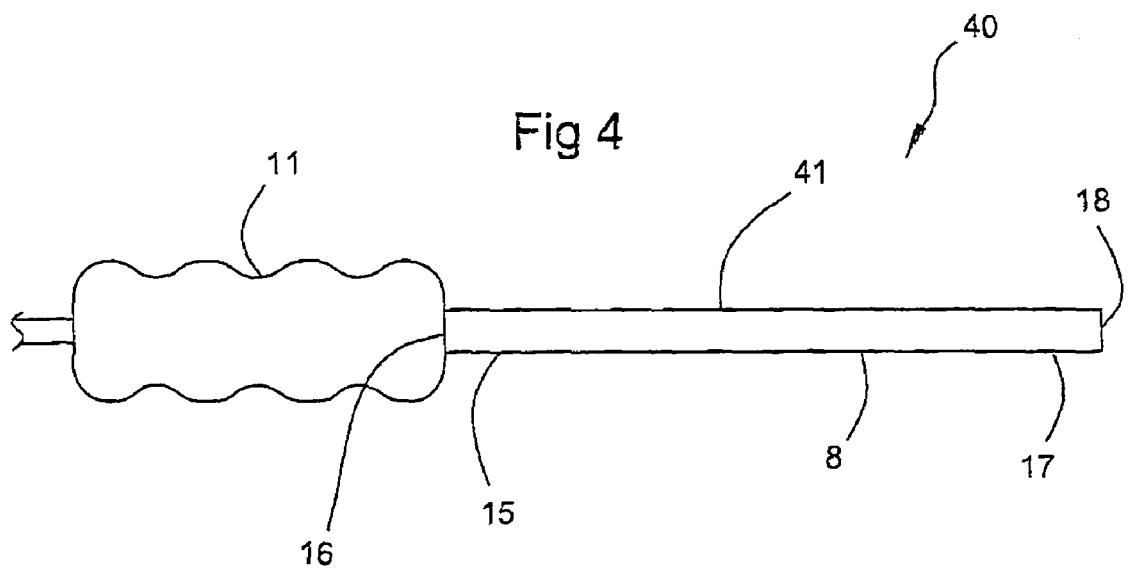
FIG. 4 is a side view of an endoscope in accordance with an embodiment of the present invention.

FIGS. 3A and 3B are side cross-sectional and front views of a distal portion 17 of an insertion member 41, and FIG. 4 is a side view of an endoscope 40 with a removable and replaceable lens cell 42, in accordance with an embodiment of the present invention. The endoscope 40 comprises an insertion member 41 and a grip 11. The insertion member 41 comprises an elongated tube 8 having a proximal portion 15 terminating at a proximal end 16 and a distal portion 17 opposite the proximal portion 15, terminating at a distal end 18, and an axial lumen extending therebetween.

Figure 1:
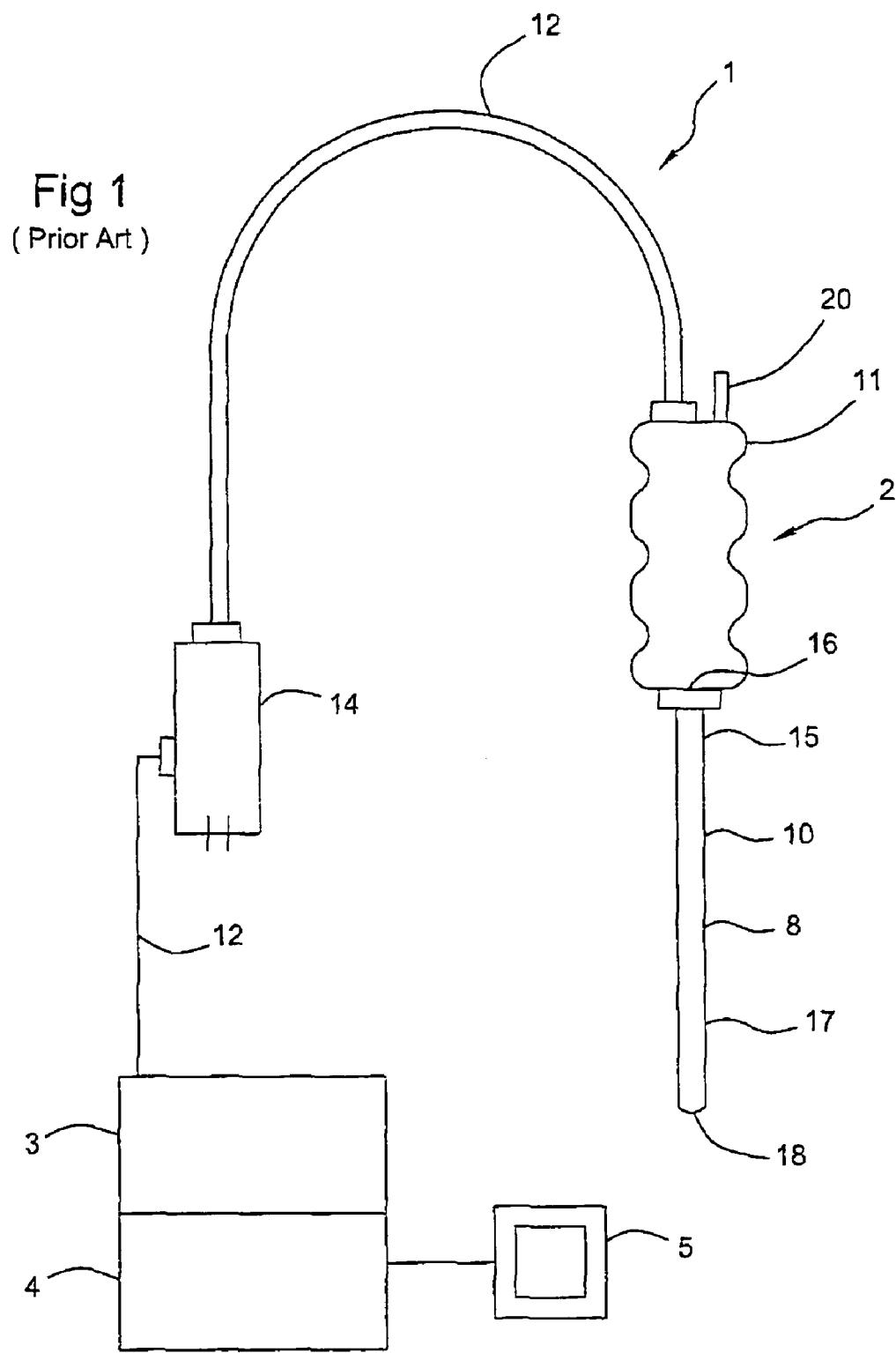
FIG. 1 illustrates an endoscope system known in the art.

The distal end portion 17 of the endoscope 2 is adapted to house an imaging system 6. The imaging system 6 comprises an imaging sensor 24, an electronic substrate 25, such as, but not limited to, a printed circuit board, and a signal cable 28. The imaging sensor 24 converts an optical image to an image signal which is communicated along the signal cable 28 to external components. Suitable imaging sensors 24 includes devices such as, but not limited to, charged coupled device (CCD) and complementary metal-oxide semiconductor (CMOS) imaging sensors 24. Illumination of a target suitable to provide an image for the imaging sensors 24 is provided in many ways, including, but not limited to, a remote light source as illustrated in FIG. 1. Alternatively, a local light source may be contained in the body of the endoscope. A suitable light source includes, but is not limited to, one or more light emitting diodes (LED).

The distal portion 17 of the endoscope 2 is adapted to also house an objective head 45. The objective head 45 comprises a removable optical window 46, a lens cell 42, a lens cell holder 44, and an optical element for directing light onto a pixilated surface of the image sensor 24, such as, but not limited to, a prism 23. The prism 23 is positioned adjacent to the imaging sensor 24 and is used to turn the image path 90 degrees as a mirror. It is appreciated to those in the art that a straight, rather than turned, optic path may be employed without deviating from the scope of the present invention.

The removable optical window 46, lens cell holder 44, lens cell 42, prism 23, and imaging sensor 24 are coupled in cooperative engagement within the distal portion 17 and are substantially aligned to a common optic axis of the objective head 45. The removable optical window 46 is located adjacent to and substantially flush with the distal end 18. The removable optical window 46 is removably coupled to the distal end 18 and replaceable to permit access to the lens cell 42. The removable optical window 46 is adapted for sealing engagement with the distal end 18 so as to protect the lens cell 42 from fluid and debris when assembled and provide access to remove and/or replace the lens cell 42 when disassembled.

The lens cell holder 44 is adapted to provide a mount or securing structure onto which the lens cell 42 is removably coupled and held in alignment with the optic axis of the objective head 45. In an embodiment in accordance with the present invention, the lens cell holder 44 is a component distinct in itself. To establish a fixed alignment and improved optical properties, the lens cell holder 44 is cemented to the prism 23.

In other embodiments in accordance with the invention, the lens cell holder 44 is integral with one or more components housed within the distal end 18. In yet other embodiments, the lens cell holder 44 is integral with the distal end portion 17.

The lens cell 42 is adapted to provide a housing for one or more optical elements 22, such as, but not limited to, lenses and/or optical filters. The optical elements 22 provide, among other things, control over the light path containing the target image. Depending on the specific optical component and/or combination of optical elements 22, the light path may be focused, directed, modified, filtered, diffused, and/or split, among other things.

In an embodiment in accordance with the present invention, the lens cell holder 44 comprises a generally tubular shape having a holder first end 50 and a holder second end 51, with an axial holder bore 52 there through. The holder bore 52 defines a lens cell holder inner surface 53 having a lens cell holder inner diameter. The lens cell holder 44 is coupled within the distal portion 17 with the holder first end 50 located adjacent the prism 23 and the holder second end 51 extending in a direction toward the distal end 18.

In an embodiment in accordance with the present invention, the lens cell 42 comprises a generally tubular shape defining a lens cell outer surface 58 having a lens cell outer diameter. The lens cell 42 further comprises a lens cell first end 55 and a lens cell second end 56, with an axial lens cell bore 57 there through. The lens cell outer diameter and the lens cell holder inner diameter are predetermined and complementary such that at least a portion of the lens cell first end 55 is adapted to be removably disposed within and in cooperative engagement with the lens cell holder bore 52. The lens cell outer surface 58 at the lens cell first end 55 is adapted to engage the lens cell holder inner surface 53 at the lens cell holder second end 51.

In one embodiment in accordance with the present invention, as shown in FIG. 3A, the lens cell outer surface 58 and the lens cell holder inner surface 53 are adapted for nesting friction engagement. The friction engagement between the lens cell outer surface 58 and the lens cell holder inner surface 53 is predetermined to substantially prevent movement there between during normal handling of the endoscope 40, while providing for disengagement. In accordance with an embodiment of the present invention, a breakable adhesive 96 is used to effect a bond between the lens cell outer surface 58 and the lens cell holder inner surface 53.

In accordance with an embodiment of the present invention, the axial position of the lens cell 42 within the lens cell holder 44 is changeable for a particular purpose. In one embodiment, the focal length of the objective head 45 is changed by changing the axial position of the lens cell 42 within the lens cell holder 44.

In another embodiment in accordance with the present invention, the lens cell 42 is held in the lens cell holder 44 by the removable optical window 46 as shown in FIGS. 3A and 3B. The optical window 46 is coupled to the distal end 18 by a breakable adhesive (not shown). A pry notch 61 provides assess to an edge of the optical window 46 to permit a tool to pry off the optical window 46.

Figure 5:
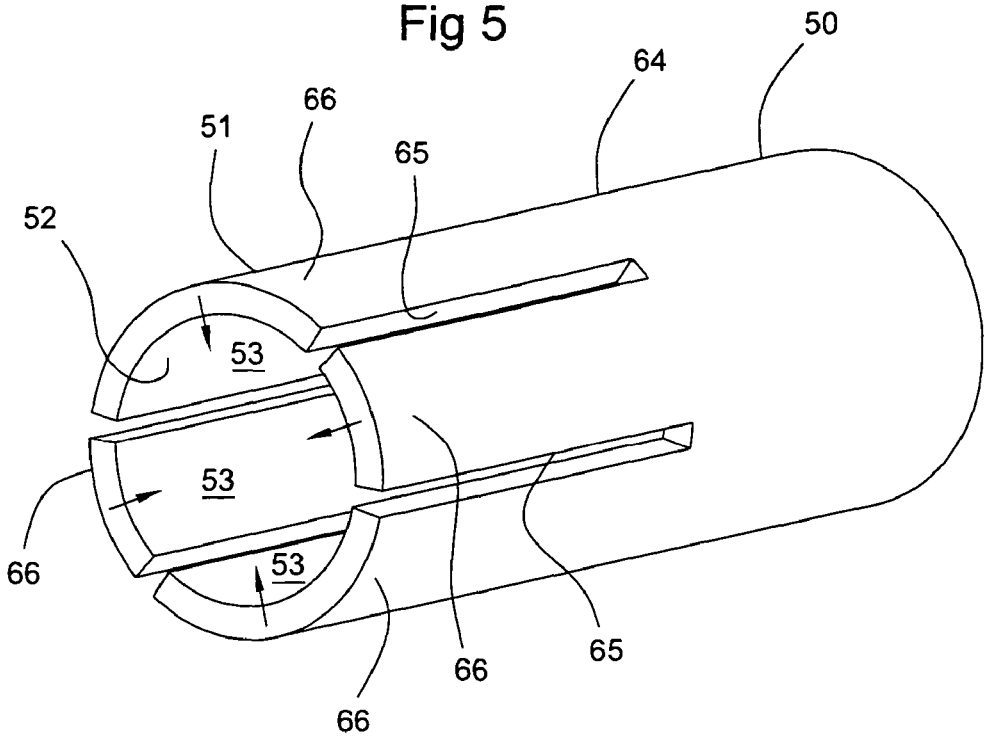
FIG. 5 is a perspective view of another embodiment of a lens cell holder in accordance with the present invention.

FIG. 5 is a perspective view of another embodiment of a lens cell holder 64 in accordance with the present invention. The lens cell holder 64 comprises one or more slits 65 extending from the second end 51 along a portion of the length of the lens cell holder 64. The slits 65 define one or more resilient lens cell holder leaves 66 that resiliently extend partially into the lens cell holder bore 52 defining a holder inner surface 53 having a diameter that is smaller than the lens cell outer diameter. The lens cell holder leaves 66 provide spring engagement with the lens cell outer surface 58 when the lens cell first end 55 extends therein.

Figure 6:
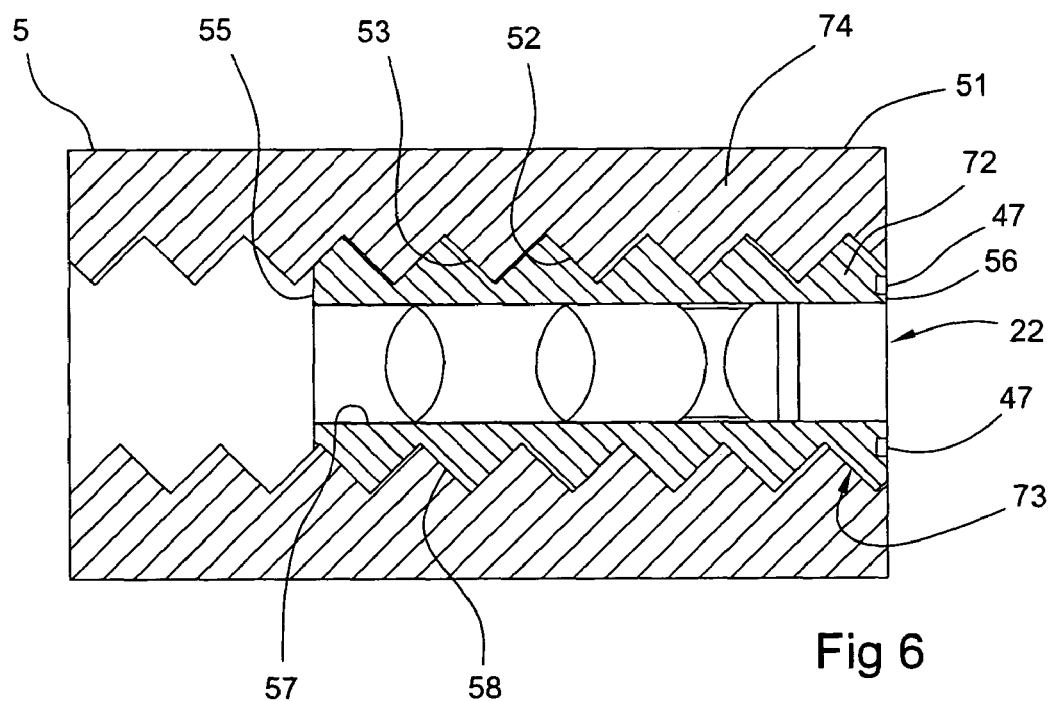
FIG. 6 is a cross-sectional view of a threaded lens cell and lens cell holder, in accordance with an embodiment of the present invention.

FIG. 6 is a cross-sectional view of an embodiment of a threaded lens cell 72 and lens cell holder 74, wherein the lens cell outer surface 58 and the lens cell holder inner surface 53 comprise complementary spiral threads 73 adapted for threaded engagement therebetween, in accordance with an embodiment of the present invention. The threaded engagement between the lens cell outer surface 58 and the lens cell holder inner surface 53 is sufficiently engaged to prevent movement between the lens cell 72 and lens cell holder 74 during normal handling of the endoscope 40, but also allow for disengagement via unthreading there with. The lens cell 72 comprises one or more tool notches 47 to provide a feature into which teeth of a tool (not shown) may engage. The teeth engage the tool notches 47 and the tool is turned to move the lens cell 72 axially by advancing the threaded lens cell 72 into or out of the lens cell holder 74.

In accordance with an embodiment of the present invention, the threaded engagement provides the capability for changing the axial position of the lens cell 72 within the lens cell holder 44 suitable for a particular purpose. In one embodiment, the focal length and/or focus of the objective head 45 is changed by changing the axial position of the lens cell 72 within the lens cell holder 44.

Figure 7A:
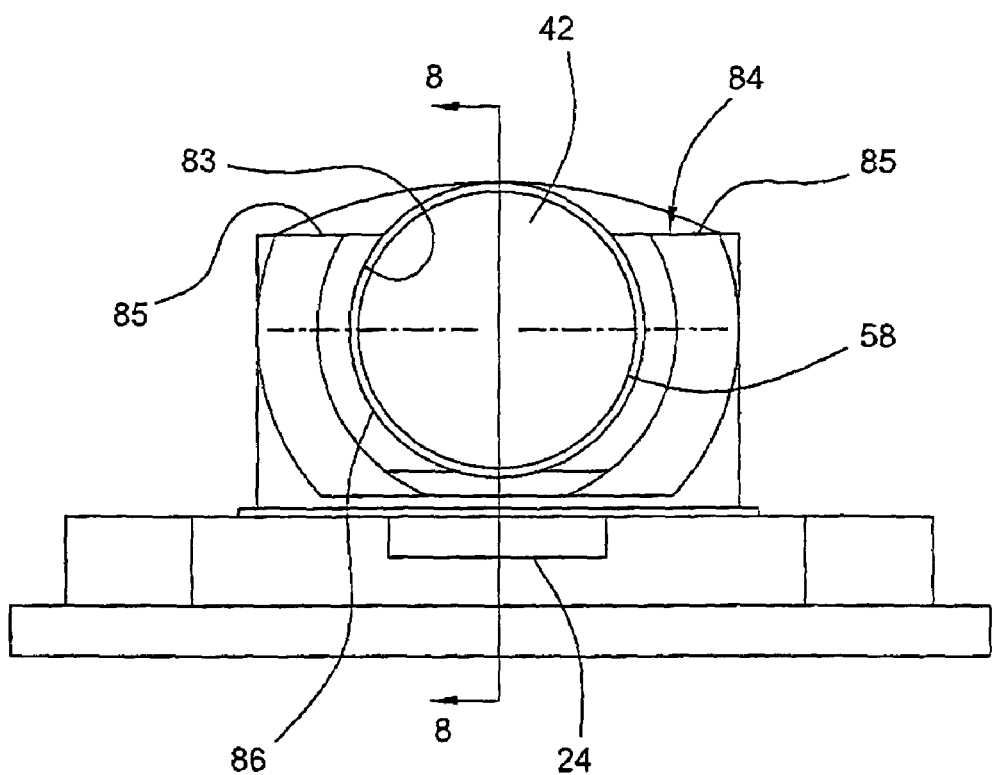
FIG. 7A is a front view of an embodiment of a C-shaped lens cell holder in accordance with the present invention.

FIG. 7A is a front view of an embodiment of a lens cell and a C-shaped lens cell holder 84 in accordance with the present invention. The C-shaped lens cell holder 84 comprises a substantially cylindrical C-shaped lens cell holder bore 83 providing sufficient surface engagement to removably couple with a lens cell 42. The C-shape provides clearance between the C-shaped lens cell holder 84 and adjacent components such as, but not limited to, the image sensor 24. In another embodiment in accordance with the present invention, the free ends 85 of the C-shaped lens holder 84 extend partially inward providing a C-shaped lens cell holder bore 83 that is smaller than the outer diameter of the lens cell 42. The free ends 85 have a predetermined resiliency that provides for spring-biased friction engagement with the lens cell outer surface 58, wherein the C-shaped lens holder inner bore 83 is adapted for friction engagement with the lens cell outer surface 58.

Figure 7B:
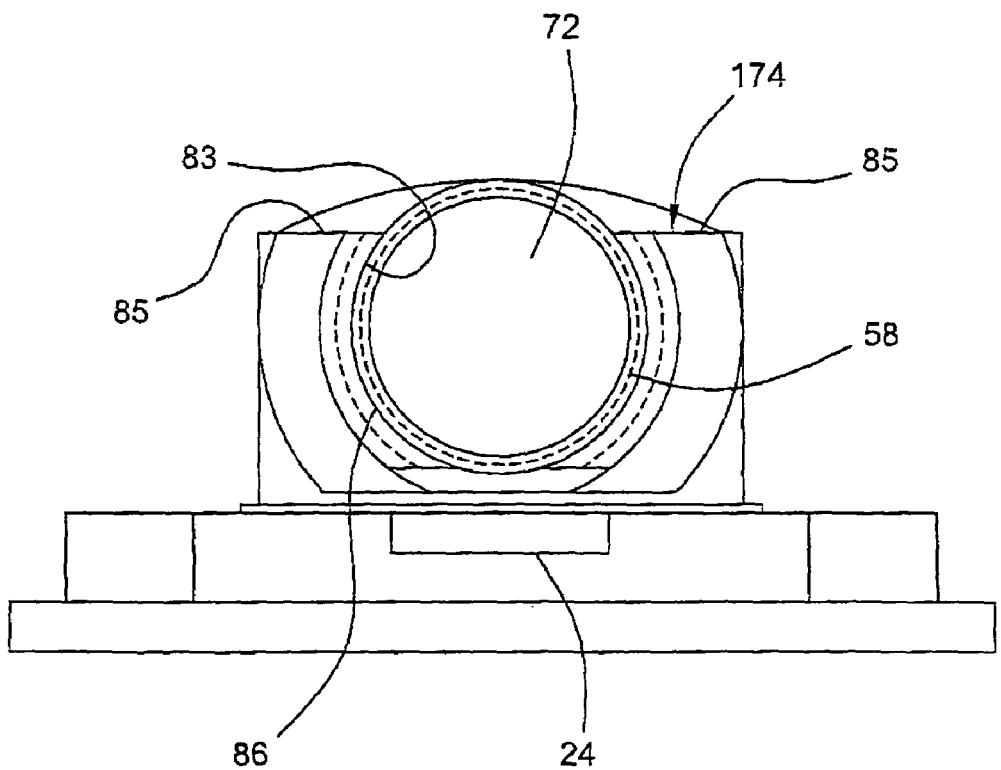
FIG. 7B is a front view of another embodiment of threaded C-shaped lens cell holder in accordance with the present invention.

FIG. 7B is a front view of a threaded C-shaped lens cell holder 174 and threaded lens cell 72, in accordance with an embodiment of the present invention. The C-shaped lens holder inner surface 83 and the lens cell outer surface 58 comprise complementary spiral threads 86, providing both threaded and spring-biased friction engagement there between.

Figure 8:
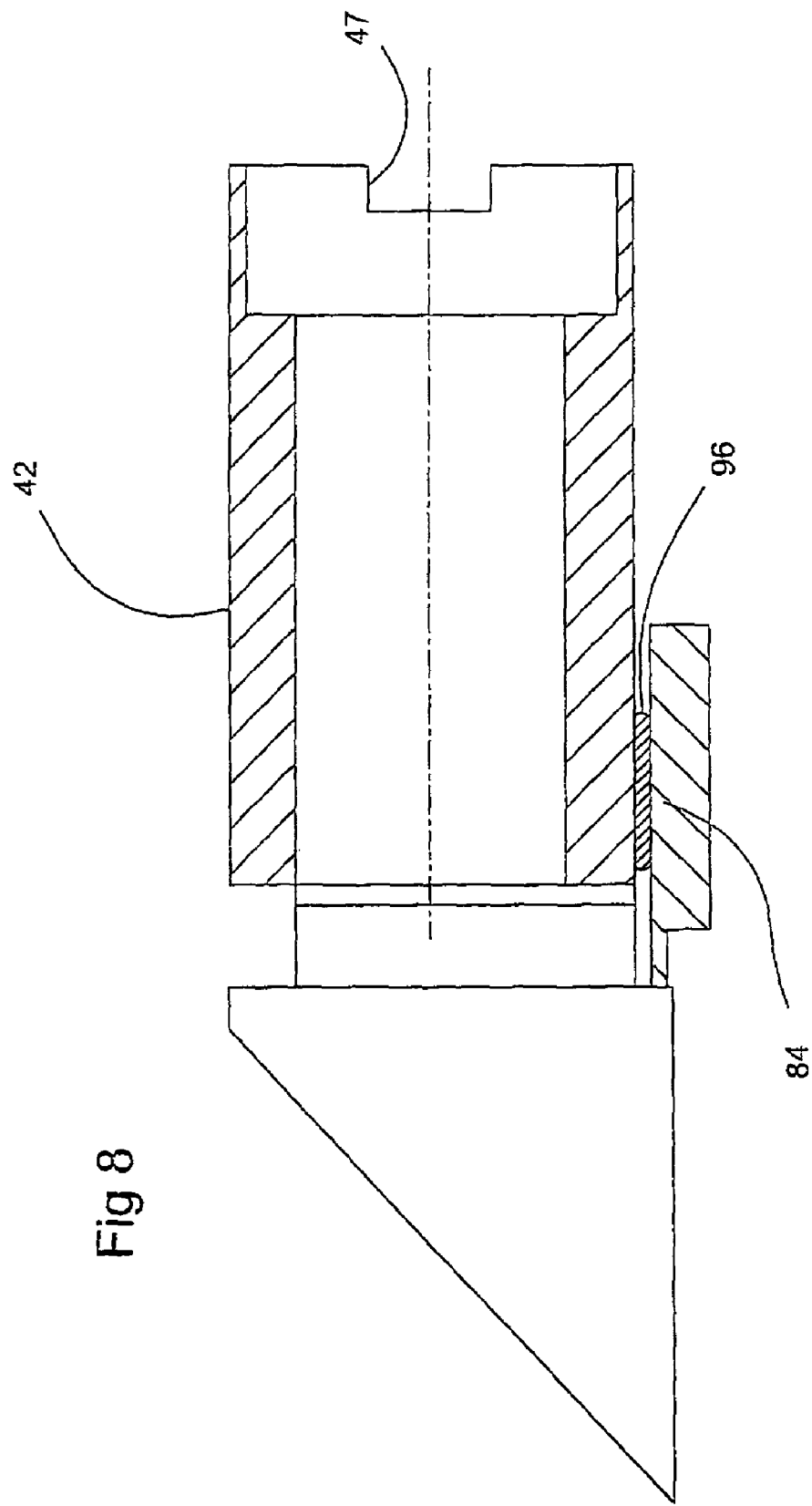
FIG. 8 is a side cross-sectional view of the lens cell and lens cell holder in accordance with the embodiment of FIG. 7A.

FIG. 8 is a side cross-sectional view of the removable lens cell 42 coupled into the C-shaped lens cell holder 84, shown in FIG. 7A, further comprising one or more tool notches 47, in accordance with an embodiment of the present invention. Tool notches 47 provide a feature into which teeth of a tool (not shown) are provided. The teeth engage the tool notches 47 and the tool is turned to effect removal of the lens cell 72 by turning the lens cell 42 relative to the lens cell holder 84, breaking the adhesive 96 (also shown in FIG. 3A). In the embodiments of FIGS. 6 and 7B, the teeth engage the tool notches 47 and the tool is turned to effect axial movement of the lens cell 72 by advancing the threaded lens cell 72 into or out of the threaded lens cell holder 174.

In the embodiment of FIG. 8, a breakable adhesive 96 is provided between the lens cell 42 and the lens cell holder 84. A breakable adhesive 96 is defined herein as one that has a predetermined sheer strength to provide for adhesive breaking or cracking using, such as, but not limited to, mechanical force and/or chemical solvents without undue harm to other components. The tool is adapted to allow for the application of sufficient force to break the bond of the adhesive 96. Similarly, the threaded engagement, such as provided by the embodiment of FIG. 6, the engagement is reinforced with a breakable adhesive 96, and still effect removal of the lens cell 42.

An embodiment in accordance with a method of the present invention for the removal of the lens cell, comprises: remove the distal window subassembly from the objective head by using a tool (not shown) and shearing the adhesive joint; unscrew the lens cell; place a new lens cell; focus an image; and cement a window subassembly back onto the objective head. In one embodiment, the window holder has recesses that are engagable with complementary pins or other engagement means on a lens wrench.

Figure 2:
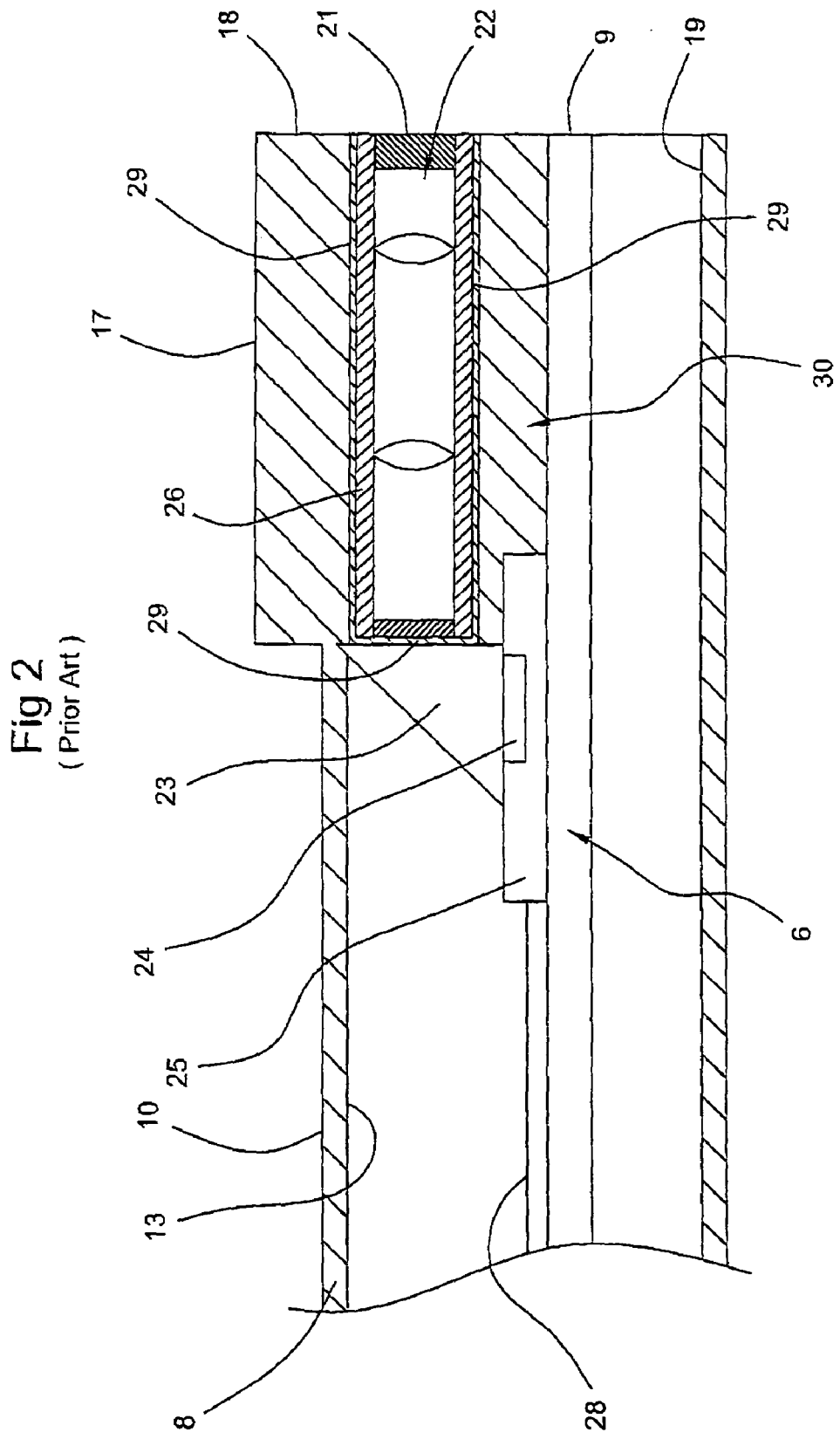
FIG. 2 is a side cross-sectional view of a distal end portion of the endoscope of FIG. 1.

FIGS. 9A and 9B are side cross-sectional and front views of a removable window holder 31, in accordance with an embodiment of the present invention. The removable window holder 31 comprises a window aperture 32 having an inward taper to hold a window 46 shown in FIG. 2A adjacent the distal end 18. The removable window holder 31 is removably coupled to the distal end 18 by breakable adhesive 96 within adhesive apertures 67. The breakable adhesive 96 is dug out of the adhesive apertures 67 permitting access by teeth on a tool (not shown) to engage the adhesive apertures and using torque, twist off the removable window holder 31.

FIG. 10 is a side cross-sectional view of a removable window holder 35, in accordance with an embodiment of the present invention. The removable window holder 35 comprises a window aperture 32 having an inward taper to hold a window 46 adjacent the distal end 18. The removable window holder 35 is removably coupled to the distal end 18 by suitable fasteners 34 that are place within fastener apertures 33. The distal end 18 comprises a window holder notch 38 having inward tapered edge 37, such that, as the window holder 35 is urged within the window holder notch 38, the inner surface 39 of the window holder 35 is urged against a face seal 36 for sealing engagement.

Figure 11A:
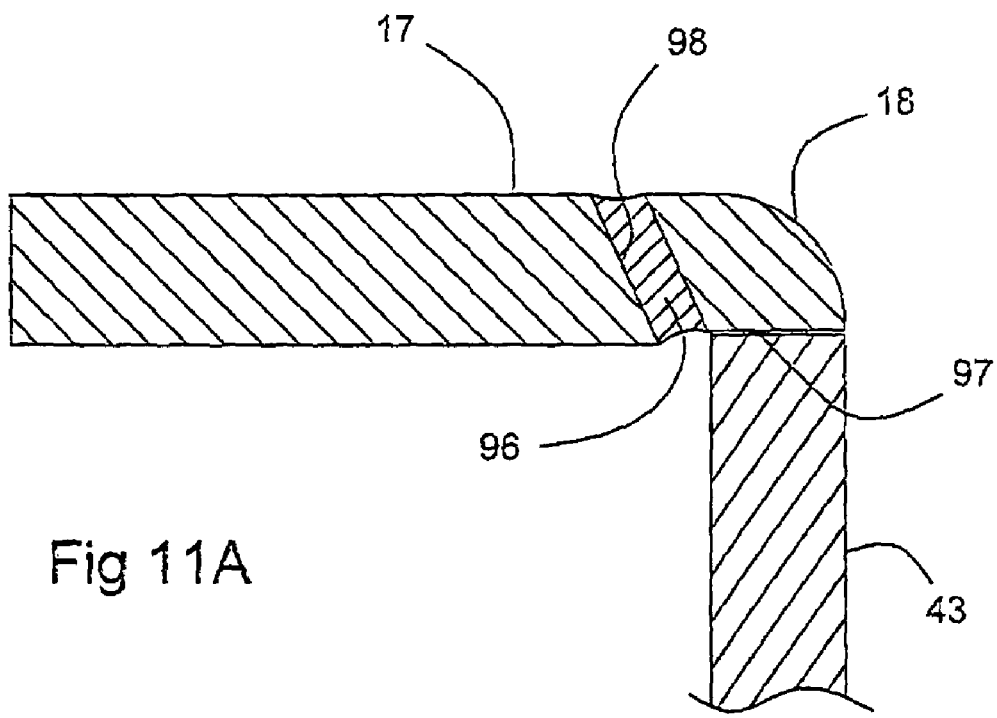
FIG. 11A is a side cross-sectional view of a portion of a distal end of an insertion member with a removable window, in accordance with an embodiment of the present invention.

FIG. 11A is a side cross-sectional view of the distal end 18 comprising a removable window holder recess 97 and a removable window 43, in accordance with an embodiment of the present invention. The removable window holder recess 97 provides a engagement, such as, but not limited to, a friction engagement and/or an adhesive engagement. A tool slot 98 is provided in the distal end portion 17 and behind the window recess 97.

Figure 11B:
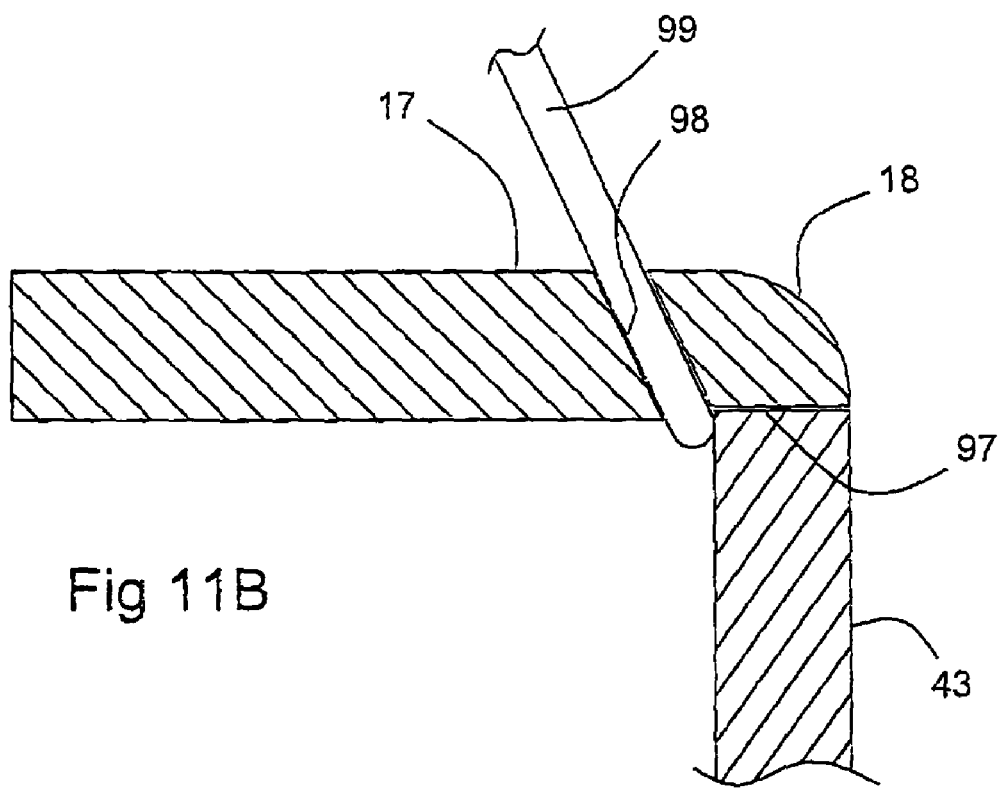
FIG. 11B is a side view of an embodiment of a working end of an engagement tool within a tool slot of the distal end of the insertion member of FIG. 11A, in accordance with an embodiment of the present invention.

FIG. 11B is a side view of an engagement tool 99 comprising a head adapted to pass through the tool slot 98 to urge against and push out the removable window 43 from the window recess 97.

The ability to remove the lens cell and interchange lens and filter elements adds versatility and extends usefulness of the endoscope. In accordance with another embodiment of the present invention, a filter is disposed within the optical path between the target and the imaging sensor. The filter is adapted to let light of a predetermined wavelength, such as, but not limited to, ultraviolet wavelength, pass through to the image sensor. In one embodiment, the filter is disposed within the lens cell as an optical element. Filters of this type are used to image biological tissue that has natural fluorescence or has been modified with a fluorescent die. Such studies can discern pathological tissue conditions, such as, but not limited to, cancer.

Persons skilled in the art will recognize that many modifications and variations are possible in the details, materials, and arrangements of the parts and actions which have been described and illustrated in order to explain the nature of this invention and that such modifications and variations do not depart from the spirit and scope of the teachings and claims contained herein.

We claim:

1. An objective head for an endoscope, wherein the objective head is located at a distal end portion of the endoscope, comprising:
  a lens cell;
  a lens cell holder, the lens cell at least partially removably coupled with at least a portion of the lens cell holder;
  wherein at least a portion of the lens cell and at least a portion of the lens cell holder are coupled in nesting, threadless frictional engagement defining a friction interface therebetween;
  wherein the portions of the lens cell and lens cell holder complement each other in size and shape so as to substantially prevent movement between the lens cell and the lens cell holder during normal handling of the endoscope, while allowing for disengagement without the need for a permanent adhesive requiring elevated temperatures to break; and
  wherein the nesting, threadless frictional engagement allows the lens cell to be removable from the lens cell holder at a distal end of the objective head.

2. An objective head for an endoscope comprising:
  a lens cell;
  a lens cell holder, the lens cell at least partially removably coupled with at least a portion of the lens cell holder;
  wherein the lens cell and the lens cell holder further comprise complementary spiral threads, the lens cell and the lens cell holder removably coupled in threaded engagement;
  a breakable adhesive disposed between the complementary spiral threads;
  wherein the lens cell comprises one or more tool notches; and
  wherein the one or more tool notches engage a tool to effect torque breakage of the adhesive and removal of the lens cell from the lens cell holder.

3. A removable lens cell for an endoscope, the endoscope having a distal end portion, comprising:

a housing adapted for mounting optical components therein, the housing adapted for removable engagement with the distal end portion;

wherein the endoscope comprises a lens cell holder, the lens cell removably coupled to the lens cell holder;

wherein at least a portion of the lens cell and at least a portion of the lens cell holder are coupled in nesting, threadless frictional engagement defining a friction interface therebetween; and wherein the portions of the lens cell and lens cell holder complement each other in size and shape so as to substantially prevent movement between the lens cell and the lens cell holder during normal handling of the endoscope, while allowing for disengagement without the need for a permanent adhesive requiring elevated temperatures to break; and wherein the nesting, threadless frictional engagement allows the lens cell to be removable from the lens cell holder at the distal end portion of the endoscope.

4. A removable lens cell for an endoscope, the endoscope having a distal end portion, comprising:

a housing adapted for mounting optical components therein, the housing adapted for removable engagement with the distal end portion;

wherein the endoscope comprises a lens cell holder, the lens cell removably coupled to the lens cell holder;

wherein at least a portion of the lens cell and at least a portion of the lens cell holder are coupled in nesting frictional engagement defining a friction interface therebetween;

wherein breakable adhesive is predisposed between the complementary spiral threads;

wherein the lens cell comprises one or more tool notches; and wherein the one or more tool notches engage a tool to effect torque breakage of the adhesive and removal of the lens cell from the lens cell holder.

* * * * *